United States Patent [19]

Hauck

[11] 4,271,021

[45] Jun. 2, 1981

[54] PROCESS FOR INCREASING THE RESISTANCE TO WATER OF PRE-COATED PREPARATIONS FOR CHROMATOGRAPHY

[75] Inventor: Heinz E. Hauck, Frankfurt am Main, Fed. Rep. of Germany

[73] Assignee: Merck Patent Gesellschaft mit Beschränkter Haftung, Darmstadt, Fed. Rep. of Germany

[21] Appl. No.: 100,330

[22] Filed: Dec. 5, 1979

[30] Foreign Application Priority Data

Dec. 23, 1978 [DE] Fed. Rep. of Germany ....... 2856056

[51] Int. Cl.$^3$ .............................................. B01D 15/08
[52] U.S. Cl. ................................ 210/198.3; 210/658; 427/341; 427/344
[58] Field of Search ......................... 210/31 C, 198 C; 427/340, 341, 344

[56] References Cited

U.S. PATENT DOCUMENTS

| 3,492,155 | 1/1970 | Baitsholts et al. | 210/198 C |
|---|---|---|---|
| 3,502,217 | 3/1970 | Bruckner | 210/198 C |
| 3,535,296 | 10/1970 | Baron et al. | 210/198 C |
| 3,922,431 | 11/1975 | Radmacher et al. | 210/198 C |
| 4,064,041 | 12/1977 | Halpaap et al. | 210/198 C |

*Primary Examiner*—John Adee
*Attorney, Agent, or Firm*—Millen & White

[57] ABSTRACT

A process for increasing the resistance to water of a chromatographic sorbent layer coated onto a support and comprising a binder of (a) salt(s) of (a) polyacrylic acid(s) and/or polymethacrylic acid(s), comprises treating the coated sorbent layer with an acid and then washing and drying the acid treated layers. The thus-prepared chromatographic materials are not only highly water resistant but also have an advantageously low impurity content.

12 Claims, No Drawings

PROCESS FOR INCREASING THE RESISTANCE TO WATER OF PRE-COATED PREPARATIONS FOR CHROMATOGRAPHY

BACKGROUND OF THE INVENTION

The present invention relates to a process for increasing the resistance to water of sorbent layers for chromatography which have been applied to supports.

Layer chromatography is becoming ever more widespread both as a rapid micro- or ultramicro-analytical method and, using thicker layers of sorbent, in preparative chemistry. The sorbents customarily used, such as silica gel, kieselguhr, aluminum oxides, magnesium silicates or surface-modified sorbents, must display an adequate adhesion to the supports under the action of mechanical stress and/or the solvents customarily used in chromatography. In order to achieve this, diverse adhesives or binders have already been proposed, for example gypsum, starch, carboxymethylcellulose or polyvinyl alcohol.

However, these known binders have the disadvantage that they either effect adequate adhesion only in very high concentration or that, when subjected to the action of corrosive reagents and, in some cases, subsequent heating, this being a procedure which is very frequently required in layer chromatography for the detection of organic substances, they become darkly colored making detection more difficult or even impossible.

In German Pat. No. 1,442,446 polyvinyl compounds containing carboxyl groups, and the salts of these compounds, which do not have these disadvantages, are described as binders. The alkali metal and alkaline earth metal salts and also magnesium salts of polyacrylic and polymethacrylic acids are mentioned as being particularly suitable; by reason of economic considerations, the sodium salts of these acids are preferred. When added to the conventional sorbents in an amount of 0.1—10% by weight, these binders give high resistance to abrasion and have good resistance to the corrosive reagents used in the detection procedures mentioned.

The polymeric binders containing carboxyl groups are employed, above all, in the form of their salts and not with free COOH groups because, in the form of salts, they have the highest viscosity in aqueous systems. They thus permit the preparation of stable suspensions of the sorbents, which suspensions do not tend to sediment during processing. Coating of supports with aqueous sorbent suspensions which contain the free polyacrylic or polymethacrylic acids as the binders is, on the other hand, difficult with respect to the preparation techniques required and results in unsatisfactory precoated preparations. The low viscosity of these suspensions makes the production by mechanical means of pre-coated preparations, for chromatography, more difficult since the sorbent already settles out as a sediment during the processing stage.

However, the layers comprising the polymeric binders containing carboxyl groups in the form of their salts have proved to possess a disadvantage, viz., a deficient resistance to water. This deficiency can be ascribed to the fact that the salts of polyacrylic and polymethacrylic acids swell extensively and dissolve in the presence of water. This, in turn, has the effect that a layer which adhered firmly beforehand, dissolves off the particular support under the action of water. However, a number of separation problems in chromatography necessitate the use of water or mixtures of water with other solvents as the solvent system. In order to enable such separations to be carried out, water-resistant sorbent layers are required, so that the development of the chromatogram is not made more difficult or even impossible by the dissolution of the layer from the particular support, which would otherwise occur. Furthermore, in sorbent layers which are not water-resistant, the binders can be partially dissolved out of the layer by the action of solvent systems which are purely aqueous or which contain water. This has a particularly adverse effect on the analytical detection of substances with $R_f$ values of more than 0.7. Moreover, in preparative layer chromatography, this effect makes it more difficult to isolate the pure substances with $R_f$ values of more than 0.7 which have been separated by the chromatography.

In order to solve specific separation problems, the sorbent layers, in layer chromatography, are frequently impregnated prior to the actual chromatography. Since the impregnating liquids are frequently in the form of purely aqueous solutions, resistance of the sorbent layers to water is required in this case also.

Water-resistant pre-coated preparations for chromatography are also necessary when, after chromatography has been carried out, detection reagents are employed in the form of their aqueous solutions to detect the individual substances which have been separated.

Furthermore, German Offenlegungsschrift No. 1,698,244 describes dispersions of crosslinkable or self-crosslinking synthetic resins or their precursors as binders for chromatographic sorbent layers. There are mentioned acrylate and methacrylate copolymers, which by copolymerization of monomers with reactive groups can also enter into subsequent reactions, as being particularly advantageous. However, in this case, due to the introduction of the additional constituents, there is an increased danger that if the reaction is not complete, very diverse substances will remain in the sorbent layer; these can be dissolved out of the layer by the action of solvent systems used in chromatography and, thus, interfere in the evaluation of the chromatogram. When polymers containing ester groups are used as binders, a hydrophobic constituent is introduced into the sorbent layer, making it more difficult to wet the layer with water. Furthermore, when sorbent suspensions which contain these ester group-containing polymers as binders are processed, their low viscosity in aqueous systems gives rise to difficulties similar to those encountered when free poly(meth)-acrylic acids are used as binders.

SUMMARY OF THE INVENTION

Accordingly, it is an object of this invention to provide a process for increasing the resistance to water of known precoated preparations for chromatography, which have been prepared using the tried and tested binders of salts of poly(meth)acrylic acids.

Upon further study of the specification and appended claims, further objects and advantages of this invention will become apparent to those skilled in the art.

These objects have been achieved by means of the present invention. Surprisingly, it has been found that a subsequent treatment of the layers which contain salts of poly(meth)acrylic acids as binders, with dilute acids results in water-resistant coatings. In this treatment, salts in the layer are converted to the corresponding free acids. The resultant polyacrylic and polymethacrylic acids virtually do not swell in water under conventional chromatographic conditions. For this reason, the structure of the layer is not changed when subjected to water. The coating is stable not only when it is entirely immersed in water for periods of up to several hours, but also when water is used as the solvent system.

The present invention thus relates to a process for increasing the resistance to water of sorbent layers for chromatography which have been applied to supports and contain, as binders, salts of poly(meth)acrylic acids, comprising treating the sorbent layer with acid and then washing and drying it.

Moreover, the invention also relates to water-resistant pre-coated preparations for chromatography, consisting essentially of sorbent layers which have been applied to supports and contain, as binders, poly(meth)acrylic acids, wherein the binders in these sorbent layers have been formed by conversion of salts of poly(meth)arylic acids in the sorbent layers by acid treatment of the binder-containing layer with subsequent washing and drying.

DETAILED DISCUSSION

Astonishingly, the pre-coated preparations for chromatography of this invention are prepared by treatment of the finished layers. The procedure is to subject the conventional pre-coated preparations for chromatography, which contain salts of polyacrylic and/or polymethacrylic acids as binders to a subsequent acid treatment, followed by cleansing and drying.

The nature of the treating acid is not critical as long as it is system compatible. Consequently in essence, all inorganic and organic acids can be used for the acid treatment. Preferably, the treating acids have anions which can be removed easily with water or lower aliphatic alcohols, including for example, hydrochloric acid, sulfuric acid, phosphoric acid, formic acid or acetic acid. Hydrochloric acid and acetic acid are particularly advantageous.

The treating acid can be employed in dilute solutions having a concentration of 0.01 to 10% by weight, preferably 0.05 to 5% by weight. The concentration necessary in a particular case will, of course, depend on the strength of the acid used and on the nature of the solvent. One of ordinary skill in the art can readily determine which is the most favorable acid concentration in a specific case by simple routine experiments, without difficulty.

The treatment can be carried out in aqueous and/or alcoholic solution. The use of dilute acids in the form of alcoholic solutions is preferred, since, in this case, the layers are wetted considerably more rapidly and more uniformly than when the treatment is carried out with aqueous acid solutions. In addition to water, preferred solvents include lower aliphatic alcohols of up to 5 C atoms, especially methanol and ethanol. Advantageously, water/alcohol mixtures over the entire mixing range can also be employed.

The acid treatment of the known conventional pre-coated preparations for chromatography, which contain salts of poly(meth)acrylic acids as binders can, for example, be effected by immersing the starting material in a dilute aqueous and/or alcoholic acid solution or by spraying the starting material with such a solution. Additionally, the treatment of the layers with dilute acids can be effected by the action of the acid solution in the gas phase. The acid solution per se can also be employed as the solvent system, i.e., the acid solution can be allowed to rise in the layer—this effect being produced by capillary forces.

The treatment time is usually a few minutes to several hours. In general, it should be at least 3 minutes and can be extended to more than 3 hours. The appropriate time depends on the strength and concentration of the acid used and on the wettability of the layer by the solvent used. In this aspect also, the best reaction conditions can be determined by routine experiments.

For washing and in order to remove excess acid, the pre-coated preparations for chromatography, treated in this way, are passed, preferably after they have been allowed to drain, through a cleansing bath. The washing bath consists essentially of a polar solvent or solvent mixture, such as, for example, water, lower aliphatic alcohols of up to 5 C atoms or mixtures of these solvents over the entire mixing range. Suitable procedures employed for washing and for removing the excess acid include the same ones used for the acid treatment, for example immersion of the materials for chromatography in the washing bath or spraying of the materials with the cleansing agent. Preferably, the materials are then dried, preferably by leaving them to stand in air, by heat treatment at up to 150° C., for example in a drying chamber, or by infrared radiation. After drying, the pre-coated preparations for chromatography of this invention are ready for use.

The fully conventional pre-coated preparations for chromatography which are employed as starting materials contain the known binders which are based on salts of poly(meth)acrylic acids. Details of these materials as well as their preparation are fully conventional. Suitable such details are discussed below.

Polymers based on acrylic and methacrylic acids are marketed, for example under the name Rohagit® (Röhm GmbH). Polymers of this type are also obtainable under the name Carbopol® (B.F. Goodrich Chemical Company). These polymers are supplied as dry, white, free-flowing powders in the form of the free acids. They have a molecular weight of about 3 to $4 \times 10^6$. For processing, they are dissolved in water and preferably converted to their salts by neutralization with bases. Salts which can be used include, in particular, the alkali metal and alkaline earth metal salts and also the magnesium salts. Usually, alkali metal salts, and in particular the sodium salts, will be employed for economic considerations. The solutions of the salts can be used at various viscosity levels. the decrease in viscosity, especially of the alkali metal salt solutions, on dilution is very slight. The aqueous solutions of the alkali metal salts are completely clear and the solutions of the alkaline earth metal salts are opaque. These solutions have a stable viscosity.

The binders are generally added in amounts of 0.1 to 10% by weight and preferably 0.5 to 5% by weight, based on the weight of the finished layer.

The starting materials may contain any of the sorbents customary in chromatography, provided they are stable to acids. Similarly, any of the conventional materials can be used as supports, glass plates being preferred. However, foils, for example made of aluminum, or plastic films are also commonly used. Very suitable conventional chromatography sorbent layers stable to acid include those of silica gels of diverse pore widths of 2–5,000 nm, kieselguhr, mixtures of silica gel and kieselguhr, aluminum oxides and magnesium silicates. The silica gels can also have modified (for example silanized) surfaces. Pre-coated preparations for chromatography, with a concentrating zone in front of the chromatography layer (compare, for example, German Offenlegungsschrift No. 2,724,569) can likewise be employed as starting materials. Also, particularly advantageously, the silica gels used for high-performance materials (compare German Offenlegungsschrift No. 2,524,065) can be employed; these silica gels have a specific surface area, based on their mass, of about 0.5 to 0.7 m²/g, an average pore diameter of about 4 to 12 nm, a pore volume of about 0.6 to 1.2 cm³/g and approximately the following particle size distribution:

< 3 μm 10 percent by weight
from 3 to 8 μm 80 percent by weight
> 8 μm 10 percent by weight.

The pre-coated preparations for chromatography, which are used as starting materials, are as a rule prepared by suspending the sorbents in spreadable, usually aqueous suspensions and, after intensive mixing and, if necessary, degassing, applying the suspensions to the supports using conventional spreading equipment or in coating installations.

These suspensions also contain the salts of polyacrylic and/or polymethacrylic acids, which salts are used as binders. Any indicators, preferably fluorescent indicators, which are optionally to be added must be stable to acid.

Preferably, magnesium tungstate is used, but calcium tungstate, strontium tungstate, barium tungstate, zinc tungstate or cadmium tungstate and also calcium molybdate are also suitable. The indicators are as a rule added in amounts of 0.5 to 5% by weight, in each case based on the finished layer. In the separating materials of this invention, as also in the conventional separating materials for chromatography, the layer thickness of the sorbent layer after drying is usually of the order of magnitude of 100 to 300 μm for analytical thin layer chromatography and up to 2 mm for preparative layer chromatography. In exceptional cases or for special applications, however, separating materials with thinner or thicker layers can also be used.

The new process offers particular advantages for the preparation of water-resistant pre-coated preparations for chromatography, especially also when compared with the possible method of directly using the free polyacrylic and/or polymethacrylic acids as binders. For example, the aqueous sorbent suspensions containing the salts of polyacrylic and/or polymethacrylic acids as binders have considerably more favorable processing characteristics during coating, because of the high viscosity achievable with these compounds. This is particularly significant in the case of large batches.

The processing of suspensions which contain the free polyacrylic or polymethacrylic acids as binders is, on the other hand, extremely difficult with regard to the preparation technique, since these suspensions are unstable and tend to sediment during processing in larger coating installations. Products prepared in this way would not meet the high demands made with regard to the quality of materials for chromatography. According to the process of this invention, on the other hand, pre-coated preparations for chromatography of extremely high quality are obtained.

In addition to providing resistance to water, the treatment of the finished layers with aqueous acid solutions, particularly when alcoholic acid solutions are employed, also effects an additional washing of organic and inorganic impurities from the layers. Such impurities, for example derived from the environment, can otherwise arise as dirt fronts when the chromatograms are developed and interfere in the evaluation. Especially in the case of substances with $R_f$ values of more than 0.7, evaluation of the chromatograms can be made impossible by these dirt fronts. Furthermore, the development times of the solvent systems are markedly lengthened by these impurities and, in the extreme case, chromatographic development can even cease because of clogging of the capillaries. Moreover, the iron content in the sorbent, especially in silica gel, is further reduced by this cleansing operation. For layers to which acid-stable fluorescent indicator has been added, this manifests itself, for example, in the form of an increased fluorescent intensity after the acid treatment. The acid treatment itself already constitutes an initial cleansing operation.

The chromatographic materials which are prepared by the process of this invention can be employed in the same way as the pre-coated preparations for chromatography which have been customary hitherto. Regarding separation efficiency and reproducibility of the separations, they are comparable with the known materials. However, the materials obtained after the additional acid treatment also have a number of advantages; for example, resistance of the coating to water, both when the entire surface is immersed in water and when water is used as the solvent system; cleansing of the sorbent layer from organic and inorganic impurities, which could interfer when evaluating the chromatograms; and increased fluorescent intensity when acid-stable indicators are used, due to a reduction in the iron content of the sorbent.

The latter two advantages of sorbent layer cleansing and increased fluorescent intensity also apply to the chromatographic materials of this invention when compared to the conventional chromatographic materials prepared directly from the free acid binders.

When separating materials prepared according to the invention are used, water or water-containing mixtures can be employed as the solvent systems in chromatography without disadvantages. Examples which may be mentioned of separations which can be carried out on these pre-coated preparations for chromatography using pure water as the solvent system include the separations of water-soluble vitamins or aminoacids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A plate rack containing 50 commercially available pre-coated plates for chromatography is immersed for 15 minutes in a vat which contains 20 liters of a 5% by weight solution of acetic acid in methanol.

The pre-coated plates (20×10 cm) for chromatography which are employed carry 175 μm thick sorbent layers on glass as the supports. The sorbent layers consist of silica gel with an average particle diameter of 5 μm, a pore volume of 0.75 ml/g and an average pore diameter of 6 nm. They contain 2.3% by weight of sodium polyacrylate (molecular weight about $3-4\times 10^6$) as the binder.

After the acid treatment, the plates are allowed to drain and are then rinsed by immersion eight times, for 15 minutes each time, in desalinated water, fresh water being used each time, and dried in air.

After chromatography using a glacial acetic acid/water mixture (15:85), the layer still adheres firmly to the substrate.

EXAMPLE 2

A plate rack containing 50 commercially available pre-coated plates for chromatography is immersed for 70 minutes in a vat which contains 20 liters of a 1% by weight solution of acetic acid in water.

The pre-coated plates (20×20 cm) for chromatography which are employed have 225 $\mu$m thick sorbent layers on glass as the support. The sorbent layers consist of 98% by weight of silica gel and 2% by weight of sodium polyacrylate (molecular weight about $3-4\times 10^6$) as the binder. The silica gel employed has an average pore diameter of 10 nm and an average particle size of 10.5 $\mu$m, with a specific surface area of 400 m$^2$/g and a pore volume of 1.0 ml/g.

After the acid treatment, the plates are allowed to drain and are then rinsed by spraying with desalinated water and dried by infrared radiation.

Even after standing in water for 3 hours, the sorbent layer still adheres firmly to the glass plate.

EXAMPLE 3

A plate rack containing 50 pre-coated plates (20×20 cm, silica gel on glass) for chromatography is immersed for 15 minutes in a vat which contains 20 liters of a 0.05% by weight solution of hydrochloric acid in methanol.

The sorbent layers of the pre-coated plates, for chromatography, which are employed consist of 96% by weight of silica gel, 2% by weight of a mixture of sodium polyacrylate and sodium polymethacrylate (1:1) as the binder and 2% by weight of magnesium tungstate as the fluorescent indicator. The silica gel employed has a specific surface area of 650 m$^2$/g, a pore volume of 0.65 ml/g, an average pore diameter of 4 nm and an average particle size of 11 $\mu$m. The layer thickness is 200 $\mu$m.

After the acid treatment the plates are allowed to drain and are then rinsed by immersion five times, for 15 minutes each time, in methanol, fresh methanol being used each time, and dried in a drying chamber at 80° C.

Even after standing in water for 5 hours, the layers adhere firmly to the substrates.

EXAMPLE 4

A plate rack containing 50 pre-coated plates for preparative layer chromatography (20×20 cm, silica gel on glass) is immersed for 50 minutes in a vat which contains 20 liters of a 1% by weight solution of hydrochloric acid in water.

The 2 mm thick sorbent layers of the pre-coated plates for preparative layer chromatography which are employed consist of 97.5% by weight of silica gel and 2.5% by weight of sodium polymethacrylate (molecular weight about $3\times 10^6$) as the binder. The silica gel employed has an average pore diameter of 6 nm and an average particle size of 25 $\mu$m.

After the acid treatment the plates are allowed to drain and are rinsed by immersion 10 times, for 15 minutes each time, in a methanol/water mixture (volume ratio 70:30), a fresh mixture being used each time, and dried by leaving to stand in air.

After a chromatographic separation using pure water as the solvent system, the layer still adheres firmly to the substrate.

EXAMPLE 5

A silica gel-coated plastic film (5 m×20 cm) for thin layer chromatography, which has been rolled up with the aid of spacers so that there is a distance of at least 2 mm between the individual windings is immersed for 40 minutes in a 3% by weight solution of acetic acid in methanol/water (1:1).

In addition to silica gel with an average particle size of 10 $\mu$m, a pore volume of 0.75 ml/g and an average pore diameter of 6 nm, the sorbent layer on the plastic film employed contains 2% by weight of sodium polymethacrylate (molecular weight about $3-4\times 10^6$) as the binder.

After the acid treatment the film is allowed to drain and is washed and dried as described in Example 1.

Even after immersion in water for 3 hours, the sorbent layer still adheres firmly to the film. The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for increasing the resistance to water and decreasing the organic and inorganic impurity content of a chromatographic sorbent layer which is coated onto a support and which comprises a binder consisting essentially of at least one salt of a polyacrylic acid, a polymethacrylic acid, or a mixture thereof, the process comprising treating the supported sorbent layer with an acid whereby the salt form of the polyacrylic acid, polymethacrylic acid, or a mixture thereof, is essentially converted to the corresponding free acid form, and the sorbent layer is cleansed from the organic and inorganic impurities; then washing the acid treated layer, whereby further cleansing from impurities is effected; and drying the acid treated layer.

2. A process of claim 1, wherein the treating acid is employed in a solution of a concentration of 0.01 to 10% by weight.

3. A process of claim 2, wherein the acid is employed in aqueous and/or alcoholic solution.

4. The process of claim 3, wherein the washing is carried out using an aqueous and/or alcoholic solution.

5. The process of claim 1, wherein the sorbent layer further comprises a fluorescent indicator.

6. A water resistant chromatographic material consisting essentially of a sorbent layer coated on a support, prepared by the process of claim 1.

7. A water resistant chromatographic material consisting essentially of a sorbent layer coated on a support, prepared by the process of claim 2.

8. A water resistant chromatographic material consisting essentially of a sorbent layer coated on a support, prepared by the process of claim 3.

9. A water resistant chromatographic material consisting essentially of a sorbent layer coated on a support, prepared by the process of claim 4.

10. A water resistant chromatographic material consisting essentially of a sorbent layer coated on a support, prepared by the process of claim 5.

11. A process of claim 1 wherein the polyacrylic acid, polymethacrylic acid or mixture thereof is not crosslinkable or self-crosslinking.

12. A material of claim 6 wherein the polyacrylic acid, polymethacrylic acid or mixture thereof is not crosslinkable or self-crosslinking.

* * * * *